(12) United States Patent
    Conrad

(10) Patent No.:    US 12,648,821 B2
(45) Date of Patent:      Jun. 9, 2026

(54) SYSTEM FOR AUTOMATICALLY TRACKING AND DISPLAYING PARAMETERS OF A JOINT DURING SURGERY

(71) Applicant: Conmed Corporation, Utica, NY (US)

(72) Inventor: Paul Conrad, Pinellas Park, FL (US)

( * ) Notice: Subject to any disclaimer, the term of this patent is extended or adjusted under 35 U.S.C. 154(b) by 630 days.

(21) Appl. No.: 17/078,730

(22) Filed: Oct. 23, 2020

(65)        Prior Publication Data

US 2021/0121247 A1     Apr. 29, 2021

Related U.S. Application Data

(60) Provisional application No. 62/924,842, filed on Oct. 23, 2019.

(51) Int. Cl.
     *A61B 34/00*        (2016.01)
     *A61B 90/00*        (2016.01)
               (Continued)

(52) U.S. Cl.
     CPC ............ *A61B 34/25* (2016.02); *A61B 90/361* (2016.02); *A61F 5/3761* (2013.01);
               (Continued)

(58) Field of Classification Search
     CPC .............. A61G 13/125; A61G 13/1245; A61G 13/123; A61G 13/0036; A61G 13/0063; A61G 7/065; A61G 7/075; A61G 7/0755; A61G 7/1082; A61G 7/1096; A61G 7/109; A61H 1/024; A61H 1/02; A61H 1/0218; A61H 1/0222; A61H 1/0237;

A61H 1/0244; A61H 1/0292; A61H 1/0296; A61F 5/37; A61F 5/37661; A61F 5/3769; A61F 5/3792; A61B 34/25; A61B 5/1121; A61B 5/4528; A61B 5/1127; A61B 5/1128; A61B 5/1114; A61B 5/742; A61B 2034/2055; A61B 2034/2059; A61B 2034/2068; A61B 2034/2057; A61B 2034/2065; A61B 34/20; A61B 34/10; A61B 90/06; A61B 90/361;
               (Continued)

(56)         References Cited

U.S. PATENT DOCUMENTS

2004/0034313 A1*   2/2004   Leitner .................. A61B 90/36
                                          600/595
2007/0249967 A1*   10/2007   Buly .................... A61B 5/1121
                                          600/595
                     (Continued)

*Primary Examiner* — Adam Baker
(74) *Attorney, Agent, or Firm* — BOND, SCHOENECK & KING, PLLC; Frederick J.M. Price

(57)          ABSTRACT

A traction system for automatically tracking and displaying parameters of a joint during surgery. The traction system includes a traction device and a computing device. The traction device has a proximal end and a distal end. The proximal end has a platform with a perineal post extending therefrom and the distal end has one or more footrests extended therefrom. One or more sensors are connected to the traction device. The one or more sensors generate sensor data based on movement of the traction device. A computing device is connected to the one or more sensors and is configured to receive the sensor data and process the sensor data into a metric. A display connected to the computing device is configured to display the metric.

10 Claims, 2 Drawing Sheets

(51) Int. Cl.

| | |
|---|---|
| *A61F 5/37* | (2006.01) |
| *A61G 13/00* | (2006.01) |
| *A61G 13/12* | (2006.01) |
| *G16H 30/20* | (2018.01) |

(52) U.S. Cl.
CPC ...... *A61G 13/0063* (2016.11); *A61G 13/1245* (2013.01); *A61G 13/125* (2013.01); *G16H 30/20* (2018.01); *A61B 2090/064* (2016.02); *A61B 2090/373* (2016.02); *A61B 2562/0219* (2013.01)

(58) Field of Classification Search
CPC .............. A61B 90/37; A61B 2090/067; A61B 2090/3612; A61B 2090/371; A61B 2090/372; A61B 2090/373
USPC ........................................................ 128/845
See application file for complete search history.

(56) References Cited

U.S. PATENT DOCUMENTS

| | | | |
|---|---|---|---|
| 2008/0081982 A1 * | 4/2008 | Simon .................... | A61B 34/25 600/407 |
| 2009/0192519 A1 * | 7/2009 | Omori .................... | A61B 34/37 606/130 |
| 2014/0188129 A1 * | 7/2014 | Kang ..................... | A61B 34/30 606/130 |
| 2015/0245971 A1 * | 9/2015 | Bernardoni ........ | A61G 13/0036 5/601 |
| 2017/0156662 A1 * | 6/2017 | Goodall ................. | A61N 2/002 |

* cited by examiner

SYSTEM FOR AUTOMATICALLY TRACKING AND DISPLAYING PARAMETERS OF A JOINT DURING SURGERY

CROSS-REFERENCE TO RELATED APPLICATION

The present application relates and claims priority to U.S. Provisional Application No. 62/924,842 filed Oct. 23, 2019, the entirety of which is hereby incorporated by reference.

BACKGROUND OF THE INVENTION

1. Field of the Invention

The invention relates generally to a surgical traction device and more particularly, a system for automatic detection and recordation of movements of a surgical traction device.

2. Description of Related Art

Sports and orthopedic surgeons often put a joint in traction to perform a procedure. This is typically to gain the required exposure to the joint. For example, in femoral-acetabular impingement (FAI) surgery for the hip, the patient is placed on the table, and a perineal post is inserted between the patient's legs. The patient's foot is then placed in a specially designed boot, similar to a ski boot. The patient's leg is then put in traction by pulling on the boot while the hip is stabilized by the post at the perineum. This causes the femoral head to pull away from the acetabulum, allowing the surgeon to access the target anatomy. This is also done in hip arthroplasty and other procedures.

Typically, the surgeon wants to track the total time the patient is in distraction. For a FAI case, the time of distraction is typically one hour and twenty minutes or less. Throughout the case, the surgeon needs to place and remove the traction from the patient as the case progresses in order to complete the procedure. During the procedure, the circulating nurse adjusts the leg, increasing and removing the traction. Every time the patient is placed under traction, the nurse pushes a button on the wall to start or pause a traction clock. This clock shows the time that the patient is spent in traction. The traction clock is typically displayed below another clock that shows the total elapsed during the surgical procedure.

Therefore, there is a need for a traction system that automatically detects and records traction start, stop, and elapsed times.

SUMMARY OF THE INVENTION

The present invention is directed to, inter alia, a traction system for automatically tracking and displaying parameters of a joint during surgery. In one embodiment, the traction system includes a traction device having a moveable component with one or more sensors attached thereto. The sensors generate sensor data based on movement of the moveable component. The system also includes a computing device connected to the sensors. The computing device is configured to receive the sensor data and process the sensor data into a metric. The system also includes a display connected to the computing device and configured to display the metric.

In another embodiment, the present invention is a traction system. The traction system includes a traction device and a computing device. The traction device has a proximal end and a distal end. The proximal end has a platform with a perineal post extending therefrom and the distal end has one or more footrests extended therefrom. One or more sensors are connected to the traction device. The one or more sensors generate sensor data based on movement of the traction device. A computing device is connected to the one or more sensors and is configured to receive the sensor data and process the sensor data into a metric. A display connected to the computing device is configured to display the metric.

The data transmission, communication, and any control signals between the at least one computing device, traction device, network, and any server computers are sent and received pursuant to wired or wireless communication. The wireless communication/transmission can be over a network, which can be any suitable wired or wireless network capable of transmitting communication, including but not limited to a telephone network, Internet, Intranet, local area network, Ethernet, online communication, offline communications, wireless communications and/or similar communications means. The wireless transmission can be accomplished through any wireless protocol/technology, including, but not limited to, ZigBee standards-based protocol, Bluetooth technology, and/or Wi-Fi technology. Further, this data can be encrypted as needed based on the sensitivity of the data or the location the printer, for example. The devices can be located in the same room, in a different room in the same building, and/or in a completely different building and location from each other. A user using a host computer (or a different computer) can send data transmission, control or communication signals to instruct the printer to merge any incomplete parts/portions of security feature(s) to form a fully formed complete security feature, and/or to print a particular fully formed complete security feature (e.g., a particular pantograph loaded in memory of the printer) on a media substrate, and to merge the particular security feature with variable data.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
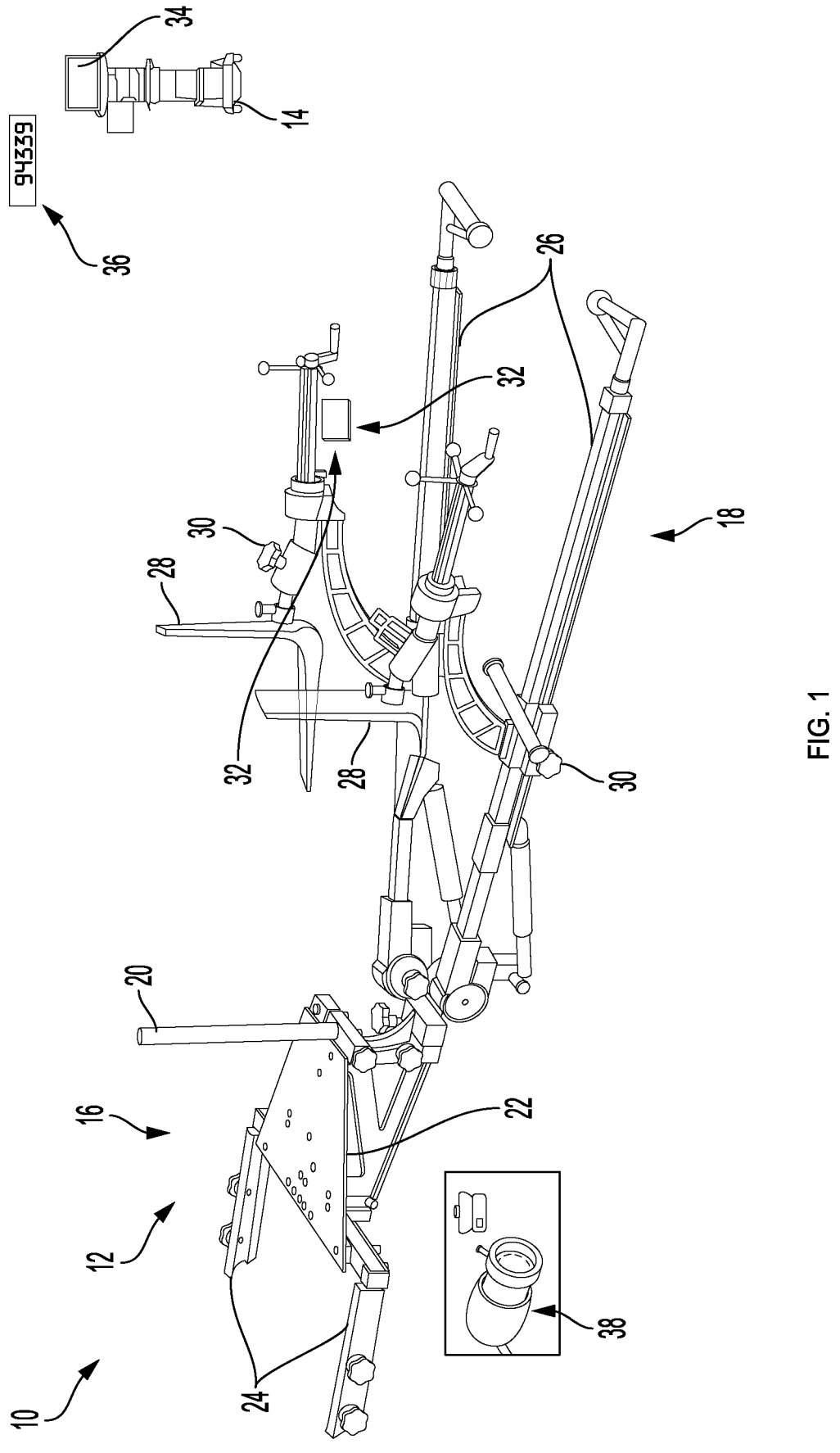
FIG. 1 is a perspective view of a traction system, according to an embodiment.

Referring now to FIG. 1, there is shown a perspective view of a traction system 10, according to an embodiment. The traction system 10 includes a traction device 12 connected to a computing device 14 via a wired or wireless connection.

In FIG. 1, the traction device 12 includes a proximal end 16 and a distal end 18. The proximal end 16 of the traction device 12 includes a platform 22 having a perineal post 20 extending therefrom. The perineal post 20 extends substantially perpendicular to the platform 22. The platform 22 has a pair of substantially parallel arms 24 extending therefrom. The arms 24 are configured to connect to or engage with a surgical bed or table (not shown). In use, the patient's lower body is positioned over or on the platform 22 such that the perineal post 20 is between the patient's legs.

Still referring to FIG. 1, the platform 22 of the traction device 12 has a pair of legs 26 extending therefrom. As shown, the legs 26 of the traction device 12 extend at angle such that, in use, the legs 26 are less than 90 degrees apart. Each leg 26 comprises a footrest 28 connected thereto. The footrest 28 is connected to and positioned above the leg 26 such that a portion of the footrest 28 is substantially aligned with the platform 22. In use, the patient's legs are extended along the legs 26 of the traction device 12 and the patient's feet at placed within the footrests 28. The traction device 12 has a plurality of adjustment mechanisms 30 attached to the various features of the traction device 12. For example, the footrests 28 and the legs 26 have adjustments mechanisms 30 attached thereto to adjust the position of the footrests 28 along the legs 26 to accommodate the differing anatomy of various patients.

The traction device 12 comprises one or more sensors 32 for detecting changes in the patient's positioning. Changes to the patient's positioning include detecting changes to the orientation of the patient's anatomy and/or stress (tension) on the patient's anatomy. According to an embodiment, the one or more sensors 32 include inertial sensors (e.g., gyroscopes, accelerometers) and tensiometers. The sensors 32 detect changes in the orientation and stress on the patient's anatomy as sensor data. The sensor data is transmitted to a processor 15 (FIG. 2) of the computing device 14.

The computing device 14 (via its processor 15) processes the sensor data to determine metrics such as traction time, amount of traction (i.e., amount of stress or force of tension), the angles of the patient's anatomy (e.g., internal and external rotation, flexion, extension), and any other key parameters. The one or more sensors 32 can be connected to the computing device 14 via a wired or wireless connection.

Once the metrics are calculated by the processor 15, the computing device 14 (via its controller (not shown)) is configured to transmit and/or display the metrics. In an embodiment, the computing device 14 has a first display 34 connected thereto. The computing device 14 transmits the metrics to the first display 34, which in the embodiment in FIG. 1, is an arthroscopic viewing screen.

According to an embodiment, the metrics include the time the patient is spent under traction ("traction time"). The traction time metric is transmitted and displayed at the first display 34 and/or at a second display 36. In the depicted embodiment, second display 36 is a wall clock. The wall clock 36 is connected to the computing device 14 via a wired or wireless connection. According to an embodiment, the wall clock 36 automatically start/stops based on metrics (e.g., traction time) received at the computing device 14.

The computing device 14 can be programmed such that one or more of the metrics have a threshold. The first display 34 and/or the second display 36 can be configured to provide a warning to the surgeon if a metric exceeds the threshold. The warning can be a visual warning or an audio warning. For example, the first display 34 and/or second display 36 emits a warning sound (e.g., via a speaker attached thereto) when the traction time exceeds a threshold.

Figure 2:
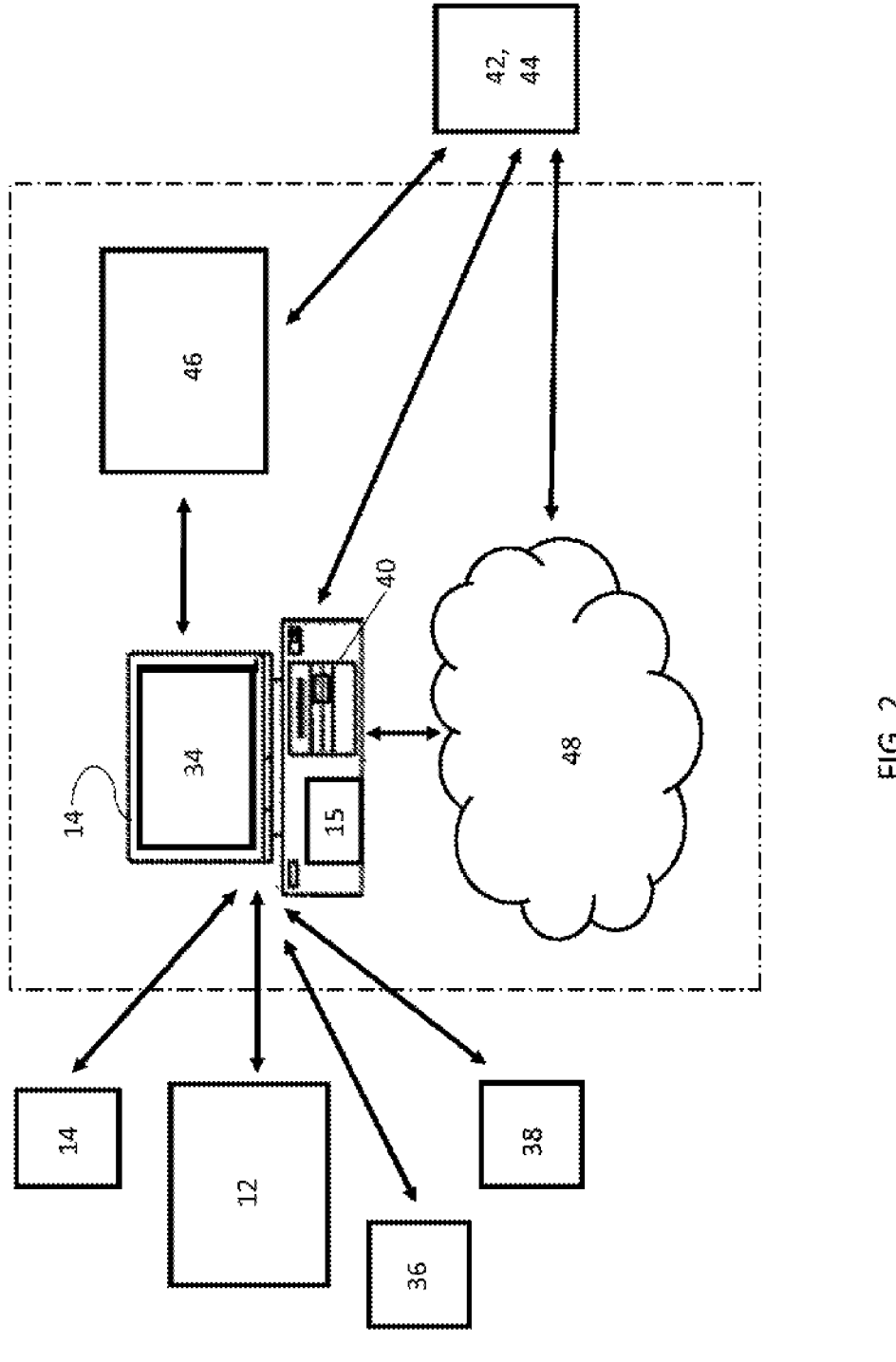
FIG. 2 is a system architecture diagram of components of the traction system including a network, server computer(s), and host computing device with various data transmission, communication, and/or control links, according to an embodiment.

The computing device 14 further comprises a memory 40. The computing device 14 records the sensor data and/or metrics by transmitting it to the memory 40. The computing device 14 transmits the sensor data and/or metrics to a digital imaging and communications in medicine (DICOM) system 42 and/or an electronic medical record 44 for tracking clinical outcomes. As shown in FIG. 2, sensor data and/or metrics can be transmitted from the computing device 14 to the network 48 or the server computer 46 before transmission to the DICOM system 42 and/or electronic medical record 44.

In an alternative embodiment, the traction device 12 additionally includes a camera 38 (FIG. 1). The camera 38 can be connected to the traction device 12 and computing device 14 via a wired or wireless connection. The camera 38 has a controller (not shown) either incorporated into the camera 38 or computing device 14. The camera 38 captures camera data, which is processed by the processor 15 of the computing device 14 into the traction time metric. The camera 38 can be operated via a controller (not shown) incorporated into the camera 38, a menu option on the computing device 14, or via a switch in the operative field.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A traction system, comprising:
a traction device having a moveable component with one or more sensors directly attached thereto;
wherein the sensors generate sensor data based on movement of the moveable component;
a computing device connected to the one or more sensors and configured to receive the sensor data and process the sensor data into a first metric, wherein the first metric is an angle of a patient's anatomy;
a camera connected to the computing device and configured to be positioned toward the traction device, wherein the camera generates camera data which is processed via the computing device into a traction time metric; and
a display connected to the computing device configured to display the first metric and the traction time metric, wherein the computing device is programmed such that each of the first metric and the traction time metric has a threshold, and the display is configured to indicate if the respective threshold is exceeded.

2. The system of claim 1, wherein the moveable component is a footrest.

3. The system of claim 1, wherein the one or more sensors comprise at least one of a gyroscope, accelerometer, and tensiometer.

4. The system of claim 1, wherein the display is an arthroscopic viewing screen.

5. The system of claim 1, wherein the display is a wall clock.

6. A traction system, comprising:
a traction device having a proximal end and a distal end, the proximal end having a platform with a perineal post extending therefrom and the distal end having one or more footrests extended therefrom;
one or more sensors directly connected to the traction device, wherein the one or more sensors generate sensor data based on movement of the traction device;
a computing device connected to the one or more sensors and configured to receive the sensor data and process the sensor data into a first metric, wherein the first metric is an angle of a patient's anatomy;
a camera connected to the computing device and configured to be positioned toward the traction device, wherein the camera generates camera data which is processed via the computing device into a traction time metric; and
a display connected to the computing device configured to display the first metric and the traction time metric, wherein the computing device is programmed such that each of the first metric and the traction time metric has a threshold, and the display is configured to indicate if the respective threshold is exceeded.

7. The system of claim 6, wherein each footrest is connected to a leg extending from the platform.

8. The system of claim 6, wherein the one or more sensors comprise at least one of a gyroscope, accelerometer, and tensiometer.

9. The system of claim 6, wherein the computing device is configured to record the first metric in its memory.

10. The system of claim 6, wherein the computing device is configured to transmit at least one of the sensor data and the first metric to an imaging system or an electronic medical record.

* * * * *